United States Patent [19]
Naoyuki et al.

[11] Patent Number: 4,827,154
[45] Date of Patent: May 2, 1989

[54] CONTROL SYSTEM FOR AIR CLEANER

[75] Inventors: Oie Naoyuki; Koyama Hiromichi, both of Kasai; Tanaka Katsuyuki, Suita; Matsumoto Shinichi, Minoo, all of Japan

[73] Assignees: Sanyo Electric Co., Ltd.; Figaro Engineering Inc., both of Osaka, Japan

[21] Appl. No.: 111,465

[22] Filed: Oct. 16, 1987

[30] Foreign Application Priority Data

Oct. 20, 1986 [JP] Japan ................. 61-248599

[51] Int. Cl.⁴ .................. H01H 35/00; F24F 7/00
[52] U.S. Cl. ....................... 307/116; 98/42.03
[58] Field of Search ........... 307/116; 98/42.03, 42.02, 98/42.04, 2.01; 340/628, 629, 630, 632, 633, 634, 577, 578, 579

[56] References Cited

U.S. PATENT DOCUMENTS

| | | | |
|---|---|---|---|
| 3,826,180 | 7/1974 | Hayashi | 98/42.03 |
| 4,352,321 | 10/1982 | Fukui et al. | 98/2.11 |
| 4,437,391 | 3/1984 | Eguchi et al. | 98/2.01 |
| 4,458,583 | 7/1984 | Fukui et al. | 98/2.01 |
| 4,478,049 | 10/1984 | Fukui et al. | 98/2.101 X |

Primary Examiner—William M. Shoop, Jr.
Assistant Examiner—Sharon D. Logan
Attorney, Agent, or Firm—Armstrong, Nikaido, Marmelstein, Kubovcik & Murray

[57] ABSTRACT

A system for controlling an air cleaner having high ability to remove smoke but low ability to remove gas with use of a gas sensor having higher sensitivity to gas than to smoke. The air cleaner is brought into operation when the gas sensor detects the gas released with the occurrence of smoke. The progress of removal of smoke is detected from the saturation of the gas sensor output, whereupon the cleaner is brought out of operation. Preferably, the air cleaner is held in operation for a predetermined period of time after the detection of the saturation to fully remove the smoke.

11 Claims, 11 Drawing Sheets (a)

(b)

(c)

CONTROL SYSTEM FOR AIR CLEANER

FIELD OF THE INVENTION

The present invention relates to the control of air cleaners with use of a gas sensor, and more particularly to a control system including a gas sensor having higher sensitivity to gas than to smoke for controlling an air cleaner which is not in balance between the ability to remove smoke and the ability to remove gas and which has higher ability to remove smoke than gas. The invention is useful for controlling air cleaners, for example, for living rooms, vehicles, etc.

Terminology

The expression an "increase in the gas sensor output" as used herein refers to a variation in the sensor output resulting from the progress of air pollution, and the expression a "decrease or reduction in the sensor output" as used herein means a variation in the sensor output resulting from the purification of air.

Prior Art

Air cleaners are known which are adapted to collect dust by high-voltage discharge or which incorporate an air filter or active carbon or like adsorbing agent. These air cleaners have the feature that the ability to remove smoke differs from the ability to remove the vapors of alcohol, other organic solvents and the like, or from the ability to remove CO, $H_2$ and like gases. Generally, these air cleaners have relatively high ability to remove smoke but low ability to remove the vapors of organic solvents such as alcohol. Further they are almost unable to remove CO, $H_2$ and like gases. For example, the active carbon adsorbing agent, which has the highest ability to adsorb solvent vapors and gases, adsorbs neither CO nor $H_2$ although adsorbing alcohol, aldehyde, etc.

These air cleaners can be initiated into a cleaning operation under the control of a gas sensor since the smoke which is chiefly produced by smoking in the interior of rooms contains gases such as CO, aldehyde, hydrogen and the like. The gas sensor detects pollution of air mainly from $H_2$ and CO entrained in the smoke. However, the gas sensor encounters difficulty in controlling the air cleaner for the termination of cleaning operation because the cleaner is imbalanced between the ability to remove smoke and the ability to remove gases and is slower to reduce the gas concentration, rendering the sensor output unable to decrease smoothly with the progress of the cleaning operation.

The prior-art techniques concerned will be described below. Unexamined Japanese Patent Publication SHO 56-131,412 discloses a system for controlling a motor vehicle air cleaner by a gas sensor. With this system, the output of the gas sensor is subjected to A/D conversion at an interval of about 1 minute to obtain reference values, and pollution is detected in terms of a variation in the sensor output from the reference value. The air cleaner, operating after the detection of pollution, is brought out of operation a period of time after a reduction in the gas sensor output.

Further according to Unexamined Japanese Patent Publication SHO 60-27,849, the minimum value of sensor output during a unit period (section) of about 6 hours is used as a reference value, and air pollution is detected from a variation in the sensor output from the reference value.

These techniques direct attention to the fact that smoking, which is the primary cause of interior air pollution, entails a sharp increase in gas concentration which is distinguishable from variations in the sensor output resulting from a lapse of time, from variations in temperature or humidity or from atmospheric pollution due to causes other than smoking.

In the case of either of these techniques, the removal of air pollutants is detected from a reduction in the sensor output. Nevertheless, when the air cleaner is primarily designed to remove smoke and has insufficient ability to remove gases, the sensor output does not decrease even after smoke has been fully removed, permitting the air cleaner to continue its operation.

SUMMARY OF THE INVENTION

The main object of the present invention is to control an air cleaner which is not in balance between smoke and gas removal abilities using a gas sensor. More specifically, it is an object of the invention to detect the completion of cleaning by a gas sensor.

According to the invention, the time to stop the operation of the air cleaner is detected from the saturation of the gas sensor output.

The saturation of the gas sensor output indicate that the increase in the sensor output per unit time no longer becomes greater than a specified value. This means that air pollution at least ceases to progress. In the usual case, this further means that smoke no longer occurs. Accordingly, when to stop the air cleaner can be detected from the saturation of the sensor output.

Saturation of the gas sensor output indicates that the gas concentration is at a constant level. To sufficiently remove smoke, it is desirable to hold the air cleaner in operation for a predetermined period of time after the detection of saturation, using suitable timer device. If the sensor output increases during the operation of the timer device, this indicates that pollution of air progresses again, so that it is desirable to continue the operation of the air cleaner by resetting the timer device. On the other hand, a reduction in the sensor output means actual purification of air, so that it is then desirable to stop the air cleaner in preference to the timer device.

Usual air cleaners operate in a plurality of modes, such as strong (high-speed operation), (medium operation) and weak (low-speed operation) modes. The operation period of the timer means may be made definite irrespective of the operation mode, or may differ for different modes. For example, when there is no great difference in a threshold value for detecting pollution between strong operation and weak operation, there is no great difference in the amount of remaining smoke therebetween when saturation is detected. In this case, therefore, it is desirable to operate the timer for a short period in a strong operation mode and for a long period in a weak operation mode. The effect of the operation of the air cleaner is dependent on the product of the operation mode and the operation period. Accordingly, instead of changing the operation period of the timer with the operation mode, the cleaner may be operated in a specified mode during the operation of the timer independently of the sensor output, with the timer operated for a definite period of time. In this case, the air cleaner is operated preferably under relatively weak conditions so as to diminish noise. Under any control conditions, the effect available is that the amount of smoke removable during the operation of the timer can be made approximately constant.

On the other hand, when there is a great difference in the threshold value for detecting pollution between different operation modes, the amount of smoke remaining when saturation is detected differs greatly with the operation mode. In this case, it is desirable to operate the timer for a long period in a strong operation mode and for a short period in a weak operation mode.

The control system of the invention for an air cleaner can be constructed of an analog circuit or digital circuit, but it is preferable to employ a digital circuit in view of the ease of processing signals. When the digital circuit is used, it is desirable to use the minimum value of sensor output in a suitable section (period) as a reference output and to use the difference or ratio between the reference output and the sensor output according to the foregoing known techniques for detecting the pollution of the atmosphere to be checked. When the reference output is to be renewed due to a change of section, it is desirable to compare a new reference output with the existing reference output so as not to renew the reference when the new reference output is greater than the existing reference output by at least a specified value. This serves to eliminate the likelihood that a sensor output resulting from a polluted atmosphere will be used as the reference output.

The sensor output obtained when the air cleaner is brought out of operation corresponds to a sensor output responsive to the cleanest air available within the capacity range of the cleaner. Accordingly, it is desirable to use as the subsequent reference output a sensor output which is obtained when the cleaner is stopped. During the operation of the cleaner, it is desired not to change the reference output irrespective of the renewal section of the reference output because if the reference output is then renewed, the reference output becomes almost equal to the sensor output, consequently stopping the air cleaner.

As is already known, the output of the gas sensor is proportional, not to the gas concentration, but to the $a$th power of the gas concentration wherein $a$ is a constant of up to 1 and is usually about 0.7 to about 0.8. This means that when the air cleaner is stopped by the operation of the timer in an atmosphere in which a gas remains, the gas sensor exhibits apparently lower sensitivity to the gas or smoke thereafter produced. When the air cleaner is stopped by the timer it is therefore desired that the variation in the sensor output from the reference output required for operating the air cleaner be made smaller.

Embodiments are given below wherein based on specific numerical conditions, signals are processed using sensor resistance which is the reciprocal of the gas sensor output. However, the embodiments are not limitative; suitably altered numerical conditions re usable, while signals can be processed by other desired method. Although the variation in sensor resistance is processed in terms of a ratio in the embodiments, a difference or the like is alternatively usable.

DESCRIPTION OF THE PREFERRED EMBODIMENTS

EMBODIMENT 1

Figure 1:
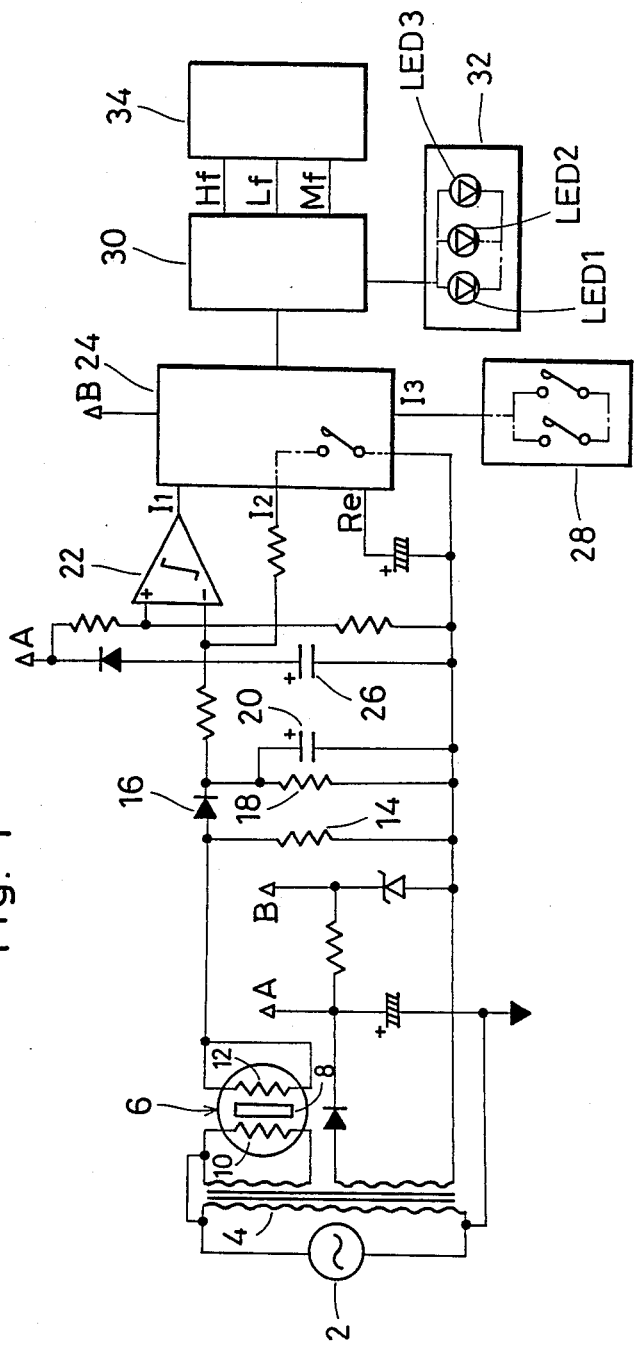
FIG. 1 is a circuit diagram showing a system embodying the present invention for controlling an air cleaner.

With reference to FIG. 1, the construction of a control system embodying the invention will be described. Indicated at 2 in the drawing is an a.c. power supply, at 4 a transformer and at 6 a gas sensor which comprises a metallic oxide semiconductor 8, such as $SnO_2$, having embedded therein an electrode 10 serving also as a heater and another electrode 12. The electrical conductivity of the gas sensor 6, which increases with the progress of air pollution, is used as its output. Indicated at 14 is a load resistance, at 16 a diode for half-wave rectification, at 18 a resistor and at 20 a capacitor which delivers the sensor output. The transformer 4 provides an unstable d.c. power supply A and a stable d.c. power supply B. The sensor 6 can be of any desired type. It may be one whose resistance value increases or which gives an increased electromotive force when exposed to polluted air.

The system further includes a comparator circuit 22, a control microcomputer 24, a capacitor 26 and a sensitivity change switch 28 which is adapted to select, for example, high sensitivity and low sensitivity. The output of the switch is fed to the microcomputer 24 through an input terminal I3. The microcomputer 24 has another input terminal I2 which is periodically grounded to release the charge of the capacitor 26. After the start of charging of the capacitor 26, the time required for the charge to reach the comparison potential of the comparator circuit 22 is counted by the microcomputer utilizing a signal available at an input terminal I1. The count is in proportion to the sensor resistance. The microcomputer 24 has a resetting terminal Re.

Indicated at 30 is an interface between the microcomputer and an air cleaner 34, and at 32 a group of light-emitting diodes for display. For example, the group is composed of a yellow light-emitting diode LED1 for displaying waiting, a green light-emitting diode LED2 for displaying cleanness and a red light-emitting diode LED3 for displaying pollution. The air cleaner 34 has three operation modes, i.e. high-speed operation Hf, medium operation Mf and low-speed operation Lf. The air cleaner 34 can also be of any desired type.

Figure 2:
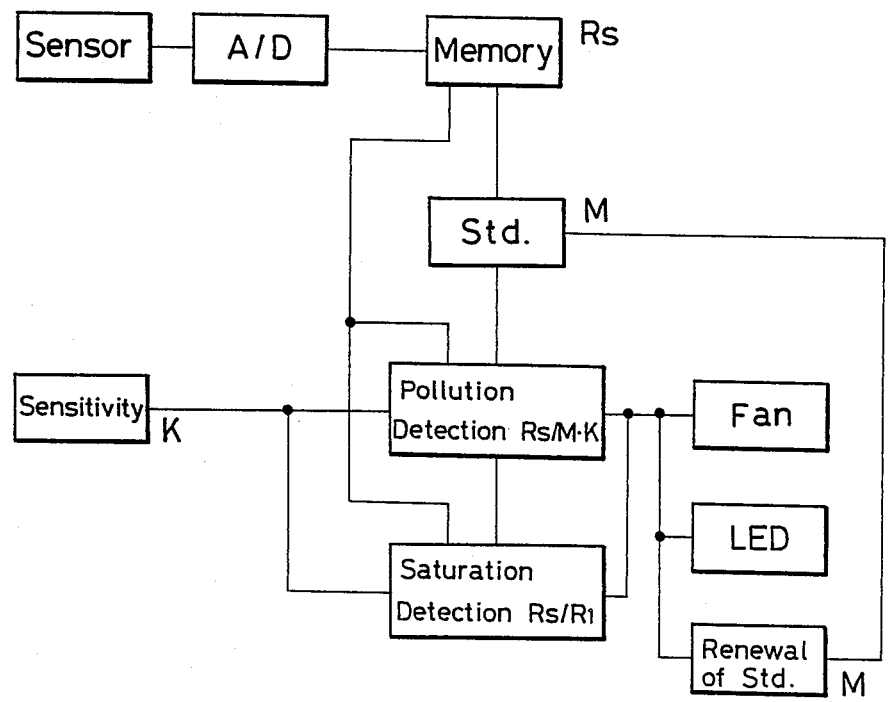
FIG. 2 is a block diagram of a microcomputer for use in the embodiment.

The construction of the microcomputer 24 will be described with reference to FIG. 2. The sensor output is subjected to A/D conversion by the comparator circuit 22, then read at all times at an interval of e.g. about 2 seconds and stored as sensor resistance Rs. The maximum of the sensor resistance, for example, the maximum thereof during a suitable period (e.g. 8 to 20 minutes), is stored as a reference value M. The sensitivity of the air cleaner is fed by the switch 28 to the microcomputer 24 as a sensitivity setting index K. For example, two sensitivity setting indices K, 1.0 (low sensitivity) and 1.2 (high sensitivity), are used. The microcomputer 24 detects the pollution of the ambient atmosphere from the ratio of the sensor resistance to the product of the reference value M and the sensitivity setting index K, i.e. Rs/(M·K). For example, the threshold value of this ratio is up to 0.5 for high-speed operation Hf, 0.5 to 0.6 for medium operation Mf and 0.6 to 0.7 for low-speed operation Lf. Table 1 shows the operating conditions for the air cleaner 34.

TABLE 1

Operating conditions for air cleaner

| | Threshold value Rs/M | | |
|---|---|---|---|
| | Low-speed operation | Medium operation | High-speed operation |
| High sensitivity (K = 1.2) | 0.84 | 0.72 | 0.6 |
| Low sensitivity (K = 1.0) | 0.7 | 0.6 | 0.5 |

Upon detection of the pollution of atmosphere, the light-emitting diode LED3 is turned on, and the air cleaner 34 is operated. During the operation of the air cleaner 34, the sensor resistance Rs is sampled, for example, at an interval of about 2 minutes to obtain a saturation output Rl. When the ratio Rs/Rl during the two-minute period is at least 0.95, saturation is detected. The saturation of the sensor output means that the gas concentration is constant and that the concentration of smoke is decreasing or that there is no further occurrence of smoke. After the detection of saturation, the air cleaner 34 is held in operation in the same mode, for example, for 20 minutes by a timer means and is thereafter brought out of operation. During the operation of the timer means, detection of saturation continues. If the saturation condition is upset with an increase in the sensor output, the timer is reset, and the operation mode is intensified as required. The saturation upsetting condition (timer resetting condition) is Rs/Rl<0.7 wherein Rl is the latest value of saturation output Rl read at an interval of two minutes. The above condition means that the timer is reset when the timer resistance decreased by at least 30% during the two minute. Thus, current progress of pollution is detected from an increase in the gas concentration to continue the operation of the air cleaner 34. Further a reduction in the sensor output means that the atmosphere has been acutally cleaned. In this case, the operation of the air cleaner is halted in preference to the timer means. Saturation is detected from Rs/Rl detected, and a timer incorporated in the microcomputer 24 provides the timer means.

The sensor resistance Rs which the air cleaner is out of operation is used as a renewed reference value M for the subsequent detection, so as to use as the reference value the actual cleaning capacity of the air cleaner or the sensor resistance which has been compensated for as to the influence of the gas present independently of smoke. If the reference value, for example, on start-up of the cleaner 34 is maintained as it is, the air cleaner 34 will not stop. Further during the operation of the air cleaner 34, a definite reference value M is to be used irrespective of the renewal section of the reference value M. If the reference value is renewed during operation, the air cleaner 34 will operate abnormally. For example, it stops in a polluted atmosphere. Table 2 shows the control conditions for the air cleaner 34 after the initiation of its operation.

TABLE 2

Control conditions for air cleaner

| | |
|---|---|
| Detection of saturation | At least 0.95 in two-minute Rs/Rl |
| Resetting | Decrease of Rs/Rl to below 0.7 |
| Intensification of operation mode | Immediately |
| Lowering of operation mode | 1 minute later |
| Stopping | 1 minute after recovery of Rs/(M · K) to at least 0.7, or 20 minutes after saturation |
| Step after stopping | Renewal of reference value M with Rs during stopping |

Figure 3:
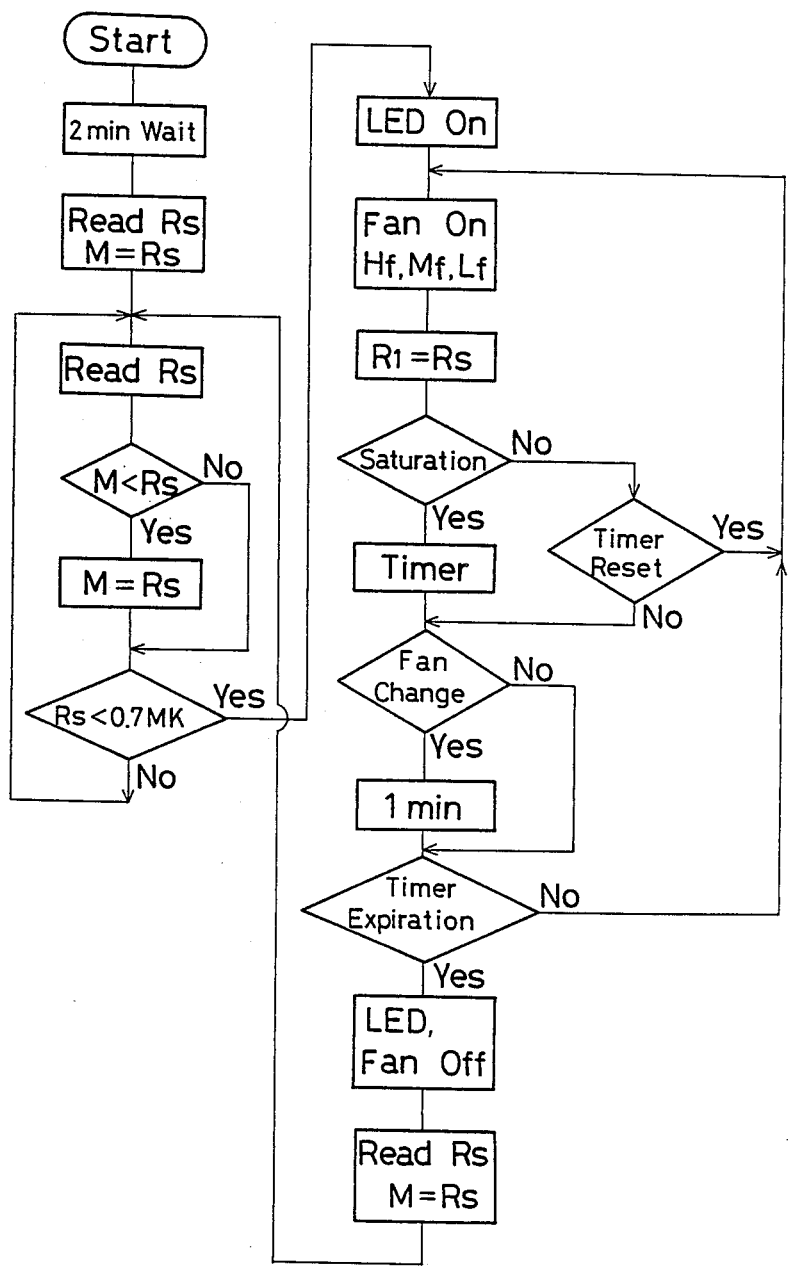
FIG. 3 is a control flow chart of the microcomputer.

The operation of the system will be described with reference to FIGS. 3 and 4. When the power supply is turned on, the light-emitting diode LED1 is turned on for two minutes, showing standby state, until the sensor 6 stabilizes. The sensor resistance Rs is thereafter read, and the read value is taken as an initial reference value M. The sensor resistance Rs is subsequently compared with the reference value M. If the sensor resistance is above the reference value, the reference value is renewed. The time point of renewal of the reference value is indicated by Q in FIG. 4. When the sensor resistance decreases to below 0.7(M.K) (0.7 is a constant determined empirically), the value is interpreted as indicating pollution. The sequence described is repeated until pollution is detected.

Upon detection of pollution, the light-emitting diode display is changed, and the operation mode of the air cleaner is determined. The operation modes available are, for example, low-speed operation Lf for 0.6<Rs/(M.K)<0.7, medium operation Mf for 0.5<Rs/(M.K)<0.6 and high-speed operation Hf for Rs/(M.K)<0.5. Upon lapse of a predetermined period of time, for example, two minutes, after the start of operation of the air cleaner, saturation output Rl is sampled, and if Rs/Rl≧0.95, saturation is detected. On detection of saturation, the timer means which is set, for example, to 20 minutes, is started to continue the operation of the air cleaner 34 during this period. When the sensor resistance varies in the meantime, the operation mode is changed according to the foregoing condition. Although the operation mode is intensified immediately after the variation, for example, from low-speed operation to medium operation, the operation mode is lowered, for example, from medium operation to low-speed operation, upon lapse of about 1 minute. Also when the sensor output drops below the level of low-speed operation, the operation is stopped after lapse of 1 minutes without utilizing the output of the timer means. Further when the sensor output increases to render the Rs/Rl ratio smaller than 0.7, for example, the timer means is reset.

The above operation will be described with reference to the solid line shown in FIG. 4 (a). (The operation of the air cleaner is shown in FIG. 4 (b), while the timer means start signal is indicated by S.) After the start of medium operation, the timer operates temporarily an is then reset due to an increase in the sensor output. After high-speed operation is then started, the timer is started. Upon lapse of the set time (at S off), the cleaner stops, whereupon the light-emitting diode display is changed, and the resulting sensor resistance is stored as a reference value. The resistance available at this time means the sensor resistance in purified air. The sensor output (at point S off) is at least the low-speed operation level relative to the original reference value. Unless the reference value is thus renewed, the air cleaner will not stop.

Figure 4:
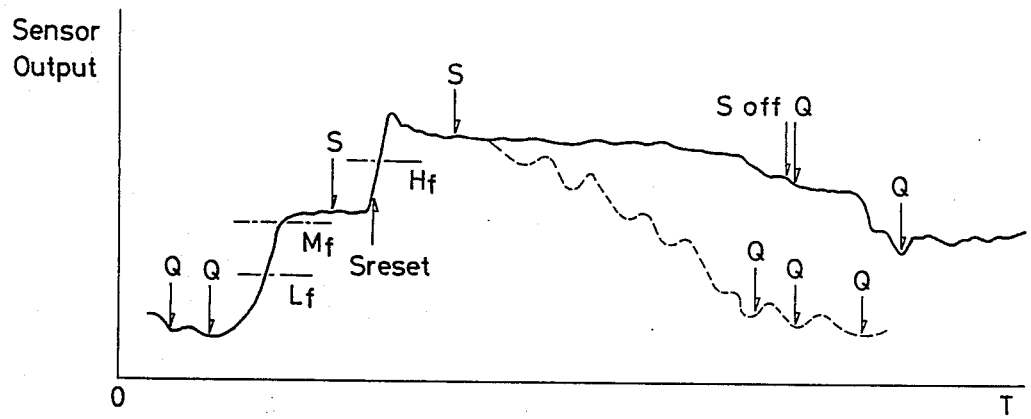
FIGS. 4 (a), (b) and (c) are waveform diagrams showing the operation characteristics of the embodiment.
Figure 4:
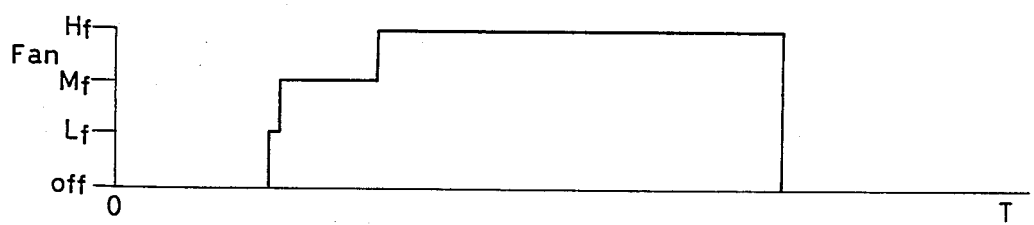
Figure 4:
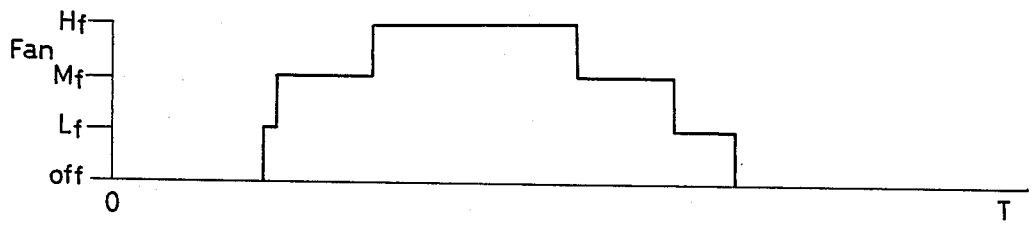

When the sensor output gradually decreases as represented by the broken line in FIG. 4 (a) (the operation of the air cleaner is shown in FIG. 4 (c)), the operation mode is lowered stepwise, with a time delay of 1 minute each time, and the sensor resistance available when the cleaner is stopped is stored as a renewed reference value.

EMBODIMENT 2

Figure 7A:
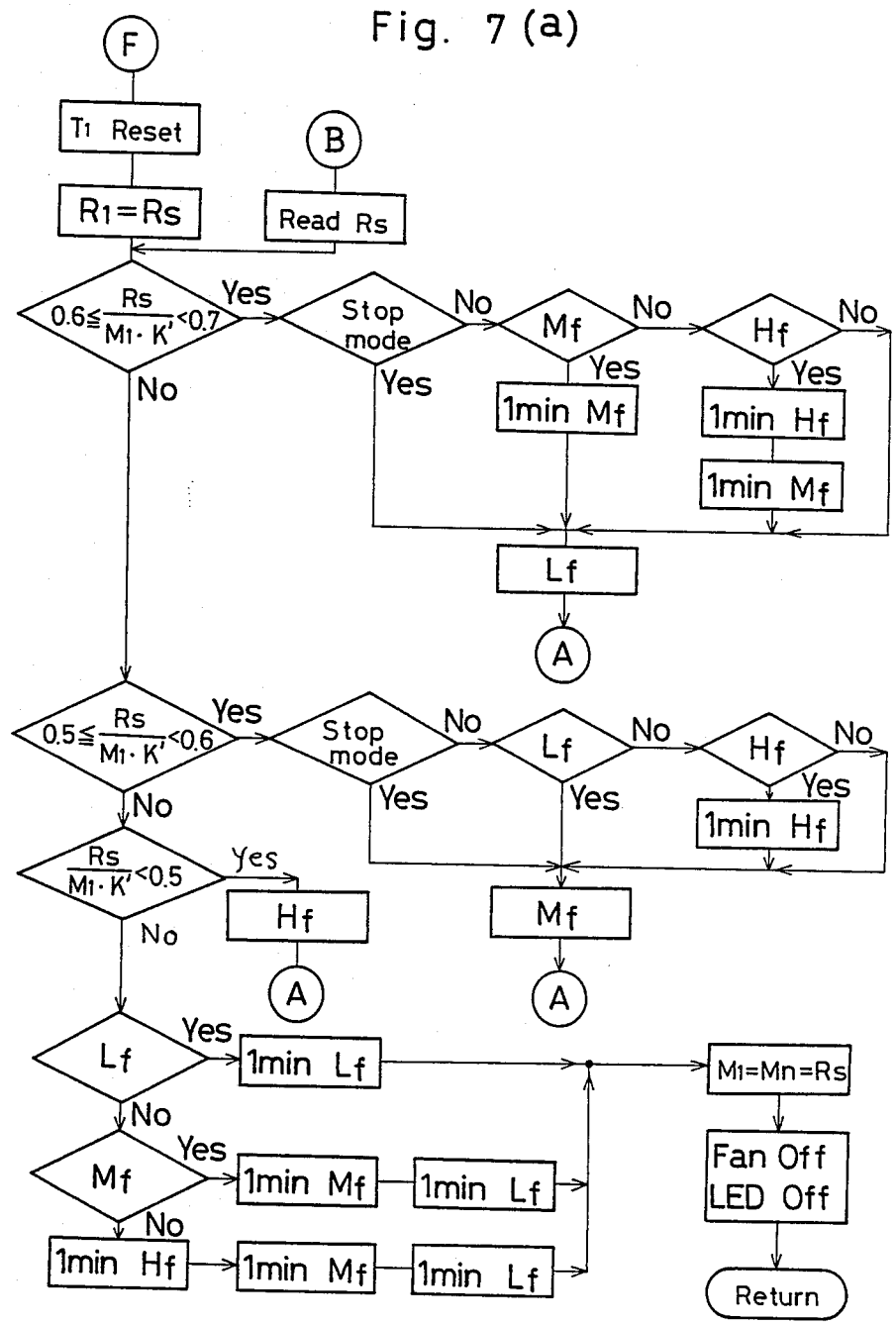
Figure 7:
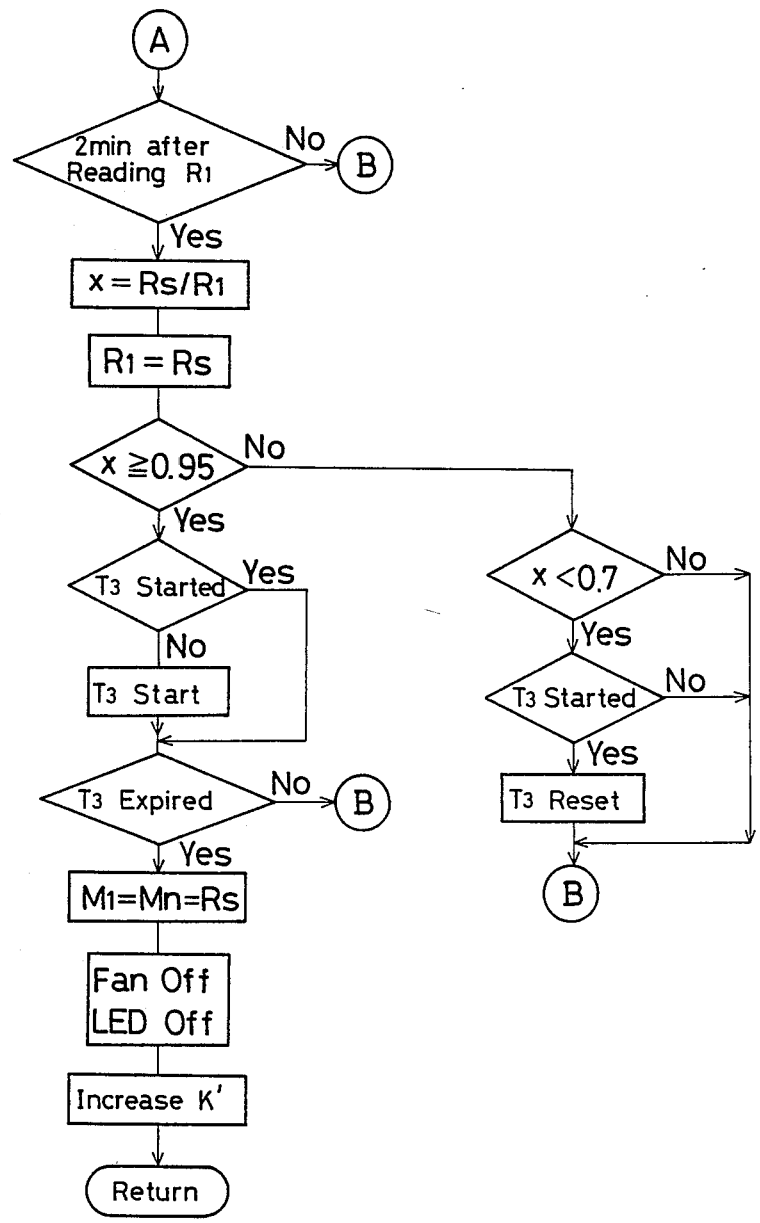
Figure 8:
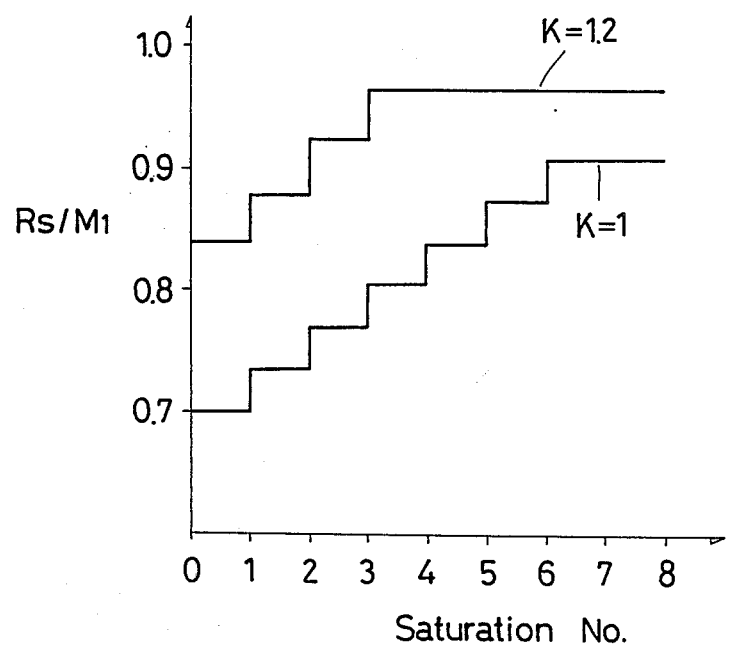
FIG. 8 is a characteristics diagram showing operation threshold values of the air cleaner relative to the frequency of saturation according to the most preferred embodiment.
Figure 9:
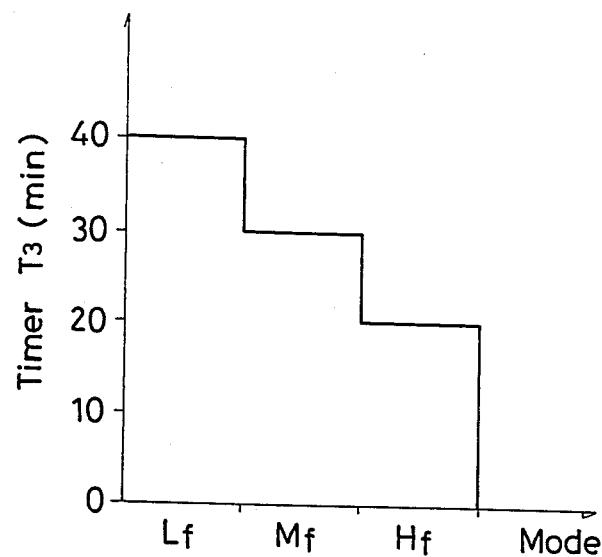
FIG. 9 is a characteristics diagram showing the relation between the operation mode and the operation period of timer means according to the most preferred embodiment.

FIGS. 5 to 9 show the most preferred embodiment. The circuit construction of this embodiment is equivalent to that shown in FIG. 1 except for the microcomputer. Further the control flow chart and operation of the system are also basically equivalent to those of the embodiment of FIGS. 1 to 4, so that the modifications will be described mainly. Thus, the present embodiment is constructed and operates in the same manner as the foregoing embodiment unless otherwise stated. Basically, the modifications are as follows. (1) The operating time of the air cleaner after the detection of saturation is made short for high-speed operation and long for lowspeed operation (FIG. 9). (2) When the air cleaner is stopped by the operation of a saturation detecting timer, the cleaner is made subsequently operable in response to smaller variations in the sensor resistance.

Figure 5:
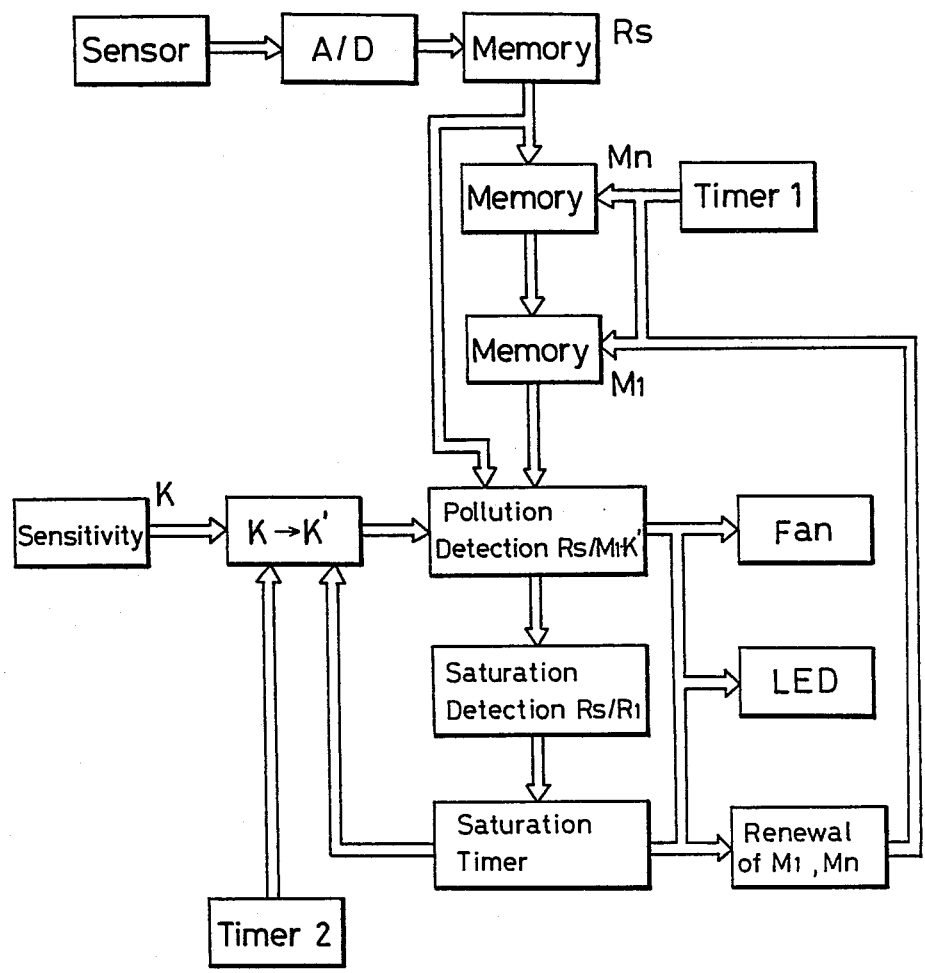
FIG. 5 is a block diagram of a microcomputer for use in the most preferred embodiment.

FIG. 5 shows the interior construction of a new microcomputer 25. A timer (timer 1) operable for about 8 to about 20 minutes, e.g. for 20 minutes in the present embodiment, is used, and this period is used at a unit section for renewing the reference value. The reference values to be used are the maximum Mn of the sensor resistance in section n (n being a natural number), and maximum Ml of the sensor resistance in section n−1 to section n. The air cleaner 34 is controlled based on the reference value Ml. The operating time of the saturation detecting timer is, for example, 20 minutes for high-speed operation mode, 30 minutes for medium operation mode and 40 minutes for low-speed operation mode. Further provided are sensitivity setting index K by the switch 28 and actual sensitivity setting index K'. When the air cleaner 34 is stopped by the timer after detection of saturation, K' is made greater than K to give increased sensitivity for detecting the pollution of the atmosphere. Further provided is a timer (timer 2) settable to about 3 to about 12 hours, e.g. 6 hours in the present case, for returning K' to K upon the lapse of this period.

Figure 6:
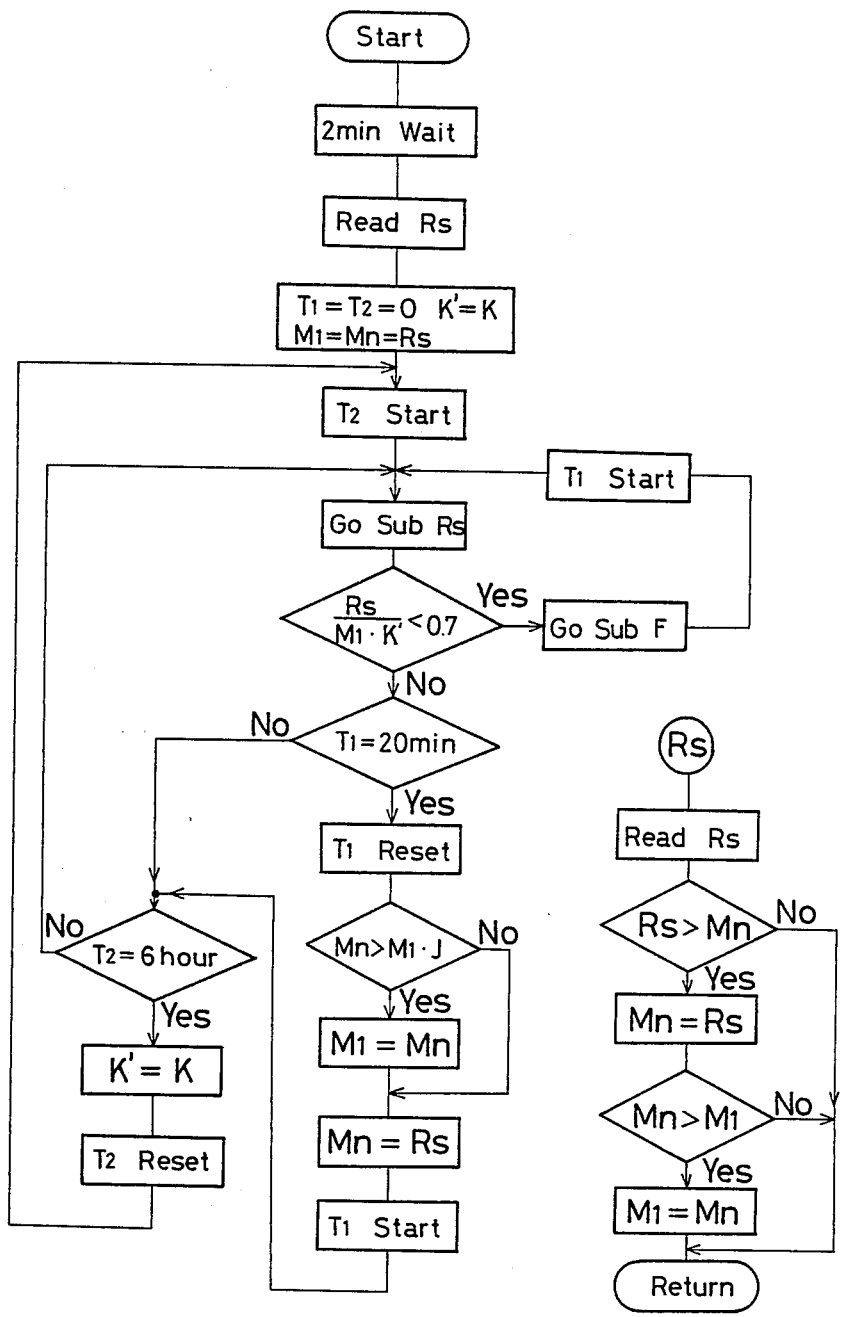
FIGS. 6 and 7 (a) and (b) are operation flow charts of the same, FIG. 6 showing the main flow chart and a sensor resistance reading subroutine, and FIGS. 7 (a) and (b) showing an overall pollution control subroutine.

FIG. 6 shows an operation flow chart. Given in Table 3 are the meanings of variables.

TABLE 3

| Variable | Meaning |
|---|---|
| T | Time, produced by the signal of a clock incorporated in microcomputer |
| n | Natural number, produced by timer 1 and representing section |
| T1 | Time of timer 1 |
| T2 | Time of timer 2 |
| Ml | Reference value for starting up air cleaner |
| Mn | Maximum of sensor resistance in section n |
| Rs | Sensor resistance |
| Rl | Sensor resistance as measured every 2 minutes after stating-up of air cleaner |
| K | Sensitivity setting index: 1.0 or 1.2 |
| K' | Actual sensitivity setting index: K' = K(1 + 0.05 m) wherein m is the number of times air cleaner is stopped by the operation of saturation detecting timer (timer 3) within 6 hours. Upon lapse of 6 hours, K' is reset to K by timer 2. When K= 1.2, the upper limit of K' is 1.38. When K= 1.0, the upper limit is 1.3 |
| Hf | High-speed operation: Rs/(Ml · K') < 0.5 |
| Mf | Medium operation: 0.5 ≦ Rs/(Ml · K') < 0.6 |
| Lf | Low-speed operation: 0.6 ≦ Rs/(Ml · K') < 0.7 |
| T3 | Saturation detecting timer: 40 minutes for low-speed operation mode, 30 minutes for medium operation mode and 20 minutes for high-speed operation mode |

When the power supply is turned on for the start of the operation of the system, the sensor resistance is read after a waiting period of 2 minutes. The variables are initialized, T1 and T2 are cleared, K is substituted for the index K', and the initial resistance Rs is substituted for Ml and Mn.

A subroutine then follows for reading the sensor resistance at an interval, for example, of about 2 seconds. In this subroutine, the sensor resistance Rs read, if greater than Mn, is substituted for Mn, and the maximum of sensor resistance in section n is taken as Mn. Further when Mn is greater than Ml, Mn is substituted for Ml.

Upon the lapse of the time (20 minutes in the present case) given by the timer 1, the value of Mn is substituted for the reference Ml, and the current sensor resistance Rs is substituted for Mn. Thus, the maximum of the sensor resistance in section n−1 to section n is taken as the reference value Ml. When Mn is lower than Ml·J due to the pollution of the atmosphere, no change is made in the reference value Ml; the previous reference value Ml is used as it is as a new reference value so as not to use the sensor resistance value corresponding to the polluted atmosphere as the reference value Ml. The value J in this case is, for example, about 0.9.

The Rs/(Ml·K') ratio, if smaller than 0.7, is interpreted as indicating the pollution of the atmosphere, whereupon the sequence proceeds to a pollution control subroutine which is shown in FIGS. 7 (a) and (b). The connector symbol A represents transfer from FIG. 7 (a) to FIG. 7 (b), while the connector symbol B represents transfer from FIG. 7 (b) to FIG. 7 (a). Upon detection of pollution, the timer 1 is reset, and the current sensor resistance Rs is read as Rl. The value Rl is thereafter renewed at an interval of 2 minutes. The operation mode of the air cleaner is then determined according to the sensor resistance value Rs, and the light-emitting diode LED3 is turned on to show pollution of the atmosphere.

The saturation detecting condition is at least 0.95 in terms of Rs/Rl, Rs being the sensor resistance 2 minutes after the reading of Rl. Upon detection of saturation, the saturation detecting timer (timer 3) is started. Further the ratio Rs/Rl, if lowering below 0.7, is interpreted as indicating new occurrence of smoke or gas, so that the timer 3 is reset. When the operation mode is to be lowered, a delay period of 1 minute is provided before the mode is changed by one step, whereas the operation mode is intensified immediately. For example, suppose Rs/(Ml·K') is 0.6 to 0.7, and the operation mode is to be changed to lowspeed operation mode. If the air cleaner is currently in stop mode, the cleaner is immediately brought into lowspeed operation mode Lf. However, if the current mode is medium operation mode Mf, the cleaner is operated in medium operation mode for 1 minute and thereafter brought into low-speed operation mode Lf. When the cleaner is currently in high-speed operation mode Hf, the cleaner is operated in high-speed operation mode Hf and then in medium operation mode Mf for 1 minute each, and was thereafter brought into low-speed operation mode Lf.

The air cleaner is brought out of operation when Rs/(Ml·K') has recovered to at least 0.7 or a sufficient period of time after the detection of saturation. The saturation detecting timer is used for detecting the time elapsed after the detection of saturation. Further when the air cleaner is to be stopped due to an increase of the sensor resistance Rs to at least 0.7(Ml·K'), a delay period of 1 minute is provided before the operation mode is lowered every step. When the air cleaner is stopped, the current sensor resistance Rs is substituted for the reference values Ml and Mn. The method of control therefor is the same as in the foregoing embodiment with the exception of the following difference.

Figure 10:
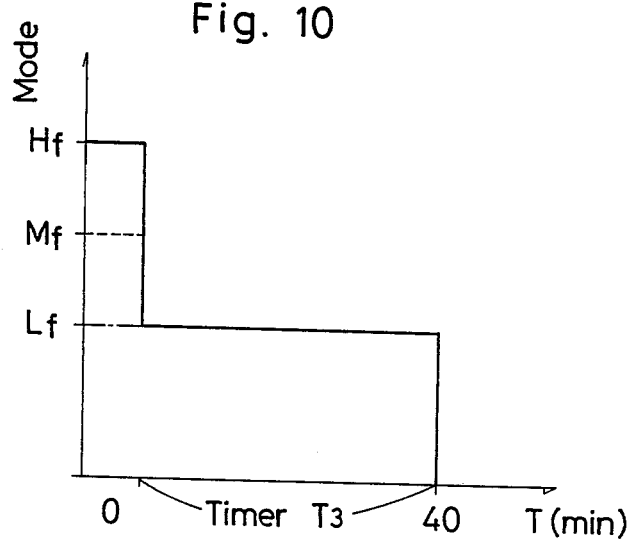
FIG. 10 is a characteristics diagram showing an operation mode during the operation of timer means according to another embodiment.

The difference is that the saturation detecting timer is operated for different periods of time for different operation modes, such that the timer is operated for a longer period of time for an operation mode of lower speed. FIG. 9 shows the relation between the timer operating time and the operation mode. This method is advantageous when the difference between the operation threshold values for the operation modes is small and there is no great difference in the amount of remaining smoke upon detection of saturation between the modes. In this case, the amount of atmosphere to be treated by the cleaner 34 after the detection of saturation is made substantially uniform to lower the smoke concentration of the atmosphere at a constant rate. Further the air cleaner 34 produces noise in high-speed operation mode, so that the period of high-speed operation is shortened in this way. Further as shown in FIG. 10, during the operating period of the saturation detecting timer, the cleaner may be operated in a particular mode independently of the sensor resistance, and the timer operated for a definite period. In this case, the operation mode is preferably low-speed or medium.

Figure 11:
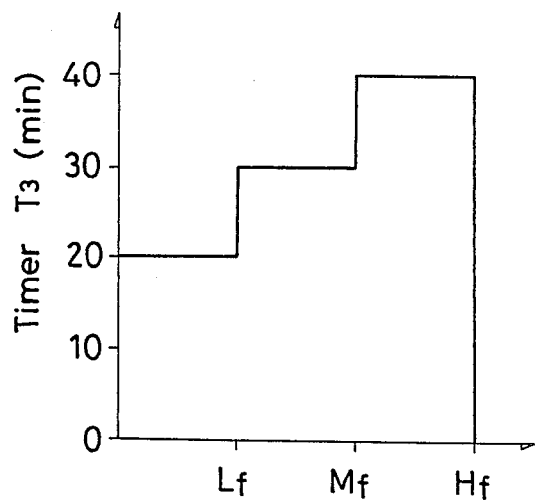
FIG. 11 is a characteristics diagram showing the relation between the operation mode and the operation period of timer means according to another embodiment.

Conversely, when the difference between the operation threshold values for different operation modes is great, it is desirable to operate the saturation detecting timer for a longer period of time in high-speed operation mode and to operate the timer for a short period in lower-speed operation mode. Because the difference between operation threshold values is great, the smoke concentration when saturation is detected is higher in higher-speed operation mode. Accordingly, the more intensified the operation mode, the longer is the saturation detecting timer operating time made so as to remove smoke sufficiently. For illustrative purposes, FIG. 11 shows the operating periods of the saturation detecting timer in this case.

When the air cleaner is brought out of operation using the saturation detecting timer, the atmosphere contains remaining gas. The gas sensitivity of the sensor 6 is in proportion not to the gas concentration but to the $\alpha$th power of the gas concentration ($\alpha$ being usually about 0.7 to about 0.8 and up to 1). It therefore follows that when a gas is produced as by smoking in the same amount as previously, the resulting variation in the sensor resistance Rs is apparently smaller than previously. We substantiated this effect by the following method. The index K was so set that the air cleaner 34 would operate when two cigarettes with smoked in a closed room. The air cleaner 34, e en when operated, almost failed to lower the gas concentration and was stopped by the saturation detecting timer. The cleaner 34 remained out of operation when two cigarettes were subsequently smoked, and thereafter operated when the third cigarette was smoked. After the air cleaner 34 was stopped again by the saturation detecting timer, additional three cigarettes were smoked, but the air cleaner 34 remained inoperative. The cleaner operated when the fourth cigarette was then smoked.

To obviate the above problem, it is desirable to change the operating conditions for the air cleaner 34 as shown in FIG. 8. Plotted as abscissa is the number of times the air cleaner 34 is stopped by the saturation detecting timer within the period of 6 hours determined by the timer 2. Plotted as ordinate is the operation threshold value of the air cleaner 34 as expressed in Rs/Ml. The air cleaner 34 is operated when this ratio is below the illustrated level.

With reference to FIGS. 7 (a) and (b) again, the flow chart therefor will be described. The number of times the air cleaner 34 is stopped by the saturation detecting timer is calculated as m, and K' is made greater than K according to the value of m. The number m is returned to 0 upon the lapse of 6 hours which is detected by the timer 2. To eliminate the likelihood that the air cleaner 34 will not stop, an upper limit is provided for K'. The upper limit is 1.38 for the high sensitivity side and 1.3 for low sensitivity side. Instead of providing the upper limit, the air cleaner 34 may be made continuously operable after the cleaner has been continuously held out of operation by the timer means. The control mode described above is based on the frequency number m within the period of 6 hours since the atmosphere of an office which is polluted by smoking during daytime will be cleaned during the nighttime due to the absence of persons, or because the atmosphere of a room polluted by smoking due to a party or the like will be cleaned by spontaneous ventilation after the end of the party.

K' can be reset to K by various other methods. For example, when the sensor resistance as measured upon stopping of the air cleaner 34 by the timer has thereafter increased by about 20 to about 40%, K' may be reset to K since the increased resistance can be interpreted as indicating the removal of the gas from the atmosphere.

In the present case, the sensitivity to detect the pollution of atmosphere is increased using K' and K. However, in the case where the air cleaner 34 is stopped by the saturation detecting timer, an Ml value greater than the actual Ml may be calculated and thereafter used in place of the actual Ml. For this purpose, for example, Ml×(1+0.05 m) or the like may be calculated from the actual reference value Ml for use in controlling the air cleaner 34.

There are various other methods for compensating for the decrease of the sensor sensitivity to occurrence of smoke at high gas concentrations. For example, we have investigated the following method. The maximum Ro of the sensor resistance after the starting-up of the system is considered. The maximum corresponds to the cleanest air experienced by the sensor, and the value Rs/Ro corresponds to the gas concentration of the atmosphere. Accordingly, the maximum Ro of the sensor resistance after the start of operation of the system is stored to vary the actual sensitivity setting index K' based on Rs/Ro. In this case, the smaller the value Rs/Ro, the higher is the gas concentration of the atmosphere, so that the value K' is increased. Further the greater the value Rs/Ro, the lower is the gas concentration of the atmosphere, so that the value K' is decreased.

Supplement

Although the embodiments described above are adapted to control a single air cleaner, the invention is not limited to these embodiments but is applicable also to the combination of air cleaner with a ventilator or an air conditioner. In this case, the ventilator is operated in preference, for example, when the temperature difference between the inside and the outside of the room is small, and the air cleaner is operated in preference when the temperature difference is great or when the air conditioner is in operation. Further for use with a motor vehicle air cleaner, the present system may be used in combination with another sensor for detecting the pollution of the outside air to effect ventilation when the outside air is clean and to operate the air cleaner when the air is polluted.

What is claimed is:

1. A system for controlling an air cleaner having higher ability to remove smoke than gas using a gas sensor, the system comprising:
   means for initiating the air cleaner into operation in response to an increase in an output of the gas sensor; and
   saturation detecting means for detecting that the increase in the gas sensor output per unit of time no longer becomes greater than a specified value so that the operation of the air cleaner is stopped.

2. A system as defined in claim 1 wherein the saturation detecting means further comprises timer means for holding the air cleaner in operation for a predetermined period of time after the detection of the saturation.

3. A system as defined in claim 2 wherein the timer means is further provided with means for resetting the timer means upon an increase in the gas sensor output.

4. A system as defined in claim 2 which further comprises means for stopping the operation of the air cleaner in preference to an output from the timer means upon detecting a reduction in the gas sensor output.

5. A system as defined in claim 2 wherein the air cleaner has at least two operation modes which are different in intensity, and the predetermined period of time for holding the air cleaner in operation by the timer means varies with the operation mode.

6. A system as defined in claim 5 wherein the predetermined period of time is short for the operation mode of higher intensity and long for the operation mode of lower intensity.

7. A system as defined in claim 2 wherein the air cleaner has at least two operation modes which are different in intensity, and the air cleaner is held in operation by the timer means in the specified one of the operation modes for the predetermined period of time.

8. A system as defined in claim 1 or 2 which comprises means for storing the minimum value of gas sensor output in a specified section while the air cleaner is out of operation, as a reference output corresponding to a clean atmosphere, and means for operating the air cleaner in response to a variation in the gas sensor output from the reference output.

9. A system as defined in claim 8 which comprises means for storing as a new reference output a gas sensor output obtained on completion of the cleaning operation.

10. A system as defined in claim 8 which comprises means for prohibiting the change of the reference output and adopting the existing reference output as a new reference output when a new reference output obtained with a change of the section is greater than the existing output by at least a predetermined value.

11. A system as defined in claim 9 which comprises means for decreasing the variation in the gas sensor output from the reference output for operating the air cleaner when the air cleaner has been stopped by the operation of the timer means.

* * * * *

UNITED STATES PATENT AND TRADEMARK OFFICE
CERTIFICATE OF CORRECTION

PATENT NO. : 4,827,154

DATED : May 2, 1989

INVENTOR(S) : Oie NAOYUKI et al

It is certified that error appears in the above-identified patent and that said Letters Patent is hereby corrected as shown below:

Column 2, line 27, "indicate" should read --indicates--;
          lines 47 and 48 "(medium operation)" should read --medium (medium operation)--.

Column 3, line 56, "re" should read --are--.

Column 5, line 65, "which" should read --when--.

Column 7, line 5, "an" should read --and--.

Column 10, line 15, "e en" should read --even--.

Signed and Sealed this

Twelfth Day of December, 1989

*Attest:*

JEFFREY M. SAMUELS

*Attesting Officer*   *Acting Commissioner of Patents and Trademarks*